(12) United States Patent
Sunor et al.

(10) Patent No.: US 12,318,181 B2
(45) Date of Patent: Jun. 3, 2025

(54) RF BASED MONITORING OF USER ACTIVITY

(71) Applicant: Nokia Technologies Oy, Espoo (FI)

(72) Inventors: Fatih Sunor, Palo Alto, CA (US); Brook Eaton, Los Altos Hills, CA (US)

(73) Assignee: Nokia Technologies Oy, Espoo (FI)

( * ) Notice: Subject to any disclaimer, the term of this patent is extended or adjusted under 35 U.S.C. 154(b) by 489 days.

(21) Appl. No.: 16/631,802

(22) PCT Filed: Jul. 13, 2018

(86) PCT No.: PCT/IB2018/055202
§ 371 (c)(1),
(2) Date: Jan. 16, 2020

(87) PCT Pub. No.: WO2019/016659
PCT Pub. Date: Jan. 24, 2019

(65) Prior Publication Data
US 2020/0170538 A1     Jun. 4, 2020

(30) Foreign Application Priority Data

Jul. 20, 2017   (EP) ..................................... 17182239

(51) Int. Cl.
*A61B 5/0507*    (2021.01)
*A61B 5/00*      (2006.01)
*A61B 5/11*      (2006.01)

(52) U.S. Cl.
CPC .......... *A61B 5/0507* (2013.01); *A61B 5/1118* (2013.01); *A61B 5/1126* (2013.01); *A61B 5/7267* (2013.01); *A61B 5/7278* (2013.01)

(58) Field of Classification Search
CPC ... A61B 5/0507; A61B 5/1118; A61B 5/1126; A61B 5/7267; A61B 5/7278; A61B 5/05;
(Continued)

(56) References Cited

U.S. PATENT DOCUMENTS 6,238,338 B1 *   5/2001   DeLuca ................. A61B 5/681
                                                    128/903
8,457,706 B2     6/2013   Baker, Jr.
(Continued)

OTHER PUBLICATIONS

Kim et al., "Tracking a Moving Target with Multipole Doppler Sensors Using an Artificial Neural Network", IEEE Antennas and Propagation Society International Symposium, Jun. 9-15, 2007 pp. 1477-1480. (Year: 2007).*

(Continued)

*Primary Examiner* — Sean D Mattson
*Assistant Examiner* — Michael Yiming Fang
(74) *Attorney, Agent, or Firm* — Joseph C. Drish; McCarter & English, LLP

(57) ABSTRACT

Methods and apparatus, including computer program products, are provided for activity tracking. In some example embodiments, there may be provided a method that includes deriving, from radio frequency based data, pseudo sensor data representative of at least an activity of a user, the pseudo sensor data derived based on at least a machine learning model configured to transform the radio frequency based data into the pseudo sensor data; and providing the pseudo sensor data. Related systems, methods, and articles of manufacture are also described.

23 Claims, 11 Drawing Sheets

(58) Field of Classification Search
CPC . A61B 5/11; G01S 13/86; G01S 13/66; G01S 13/90; G01S 13/56; G16H 50/70
See application file for complete search history.

(56) References Cited

U.S. PATENT DOCUMENTS

| | | | |
|---|---|---|---|
| 8,740,793 | B2 | 6/2014 | Cuddihy et al. |
| 9,148,483 | B1 | 9/2015 | Molettiere et al. |
| 9,549,691 | B2 | 1/2017 | Tran |
| 9,989,622 | B1* | 6/2018 | Griesdorf ............. G01S 13/878 |
| 2012/0116186 | A1 | 5/2012 | Shrivastav et al. |
| 2012/0203491 | A1* | 8/2012 | Sun ..................... A61B 5/0006 702/108 |
| 2012/0245479 | A1 | 9/2012 | Ganesh et al. |
| 2015/0164430 | A1 | 6/2015 | Hu et al. |
| 2016/0162256 | A1* | 6/2016 | Komaromi ............ H04Q 9/00 340/870.07 |
| 2017/0095181 | A1* | 4/2017 | Hauenstein ......... A61B 5/1121 |
| 2017/0097413 | A1* | 4/2017 | Gillian ................ G06F 3/011 |
| 2017/0156594 | A1* | 6/2017 | Stivoric ............. A61B 5/0008 |
| 2017/0172467 | A1* | 6/2017 | Eriksson ............ A61B 5/1118 |
| 2017/0351827 | A1* | 12/2017 | Rogers ................ G01S 7/415 |
| 2019/0186949 | A1* | 6/2019 | Yuen ................... G01C 22/006 |
| 2019/0336107 | A1* | 11/2019 | Hope Simpson ... G01S 15/8977 |
| 2020/0066130 | A1* | 2/2020 | Ten Kate .............. G06F 3/017 |

OTHER PUBLICATIONS

Attal et al., "Physical Human Activity Recognition Using Wearable Sensors" Sensors 2015, 15, 31314-31338 (Year: 2015).*

Mazurek, Paweł & Wagner, Jakub & Miękina, Andrzej & Morawski, Roman & Ciamulski, Tomasz. (2016). Using accelerometers for evaluation of measurement uncertainty in impulse-radar system for monitoring of elderly and disabled persons. (Year: 2016).*

M. A. Alsheikh, S. Lin, D. Niyato and H.-P. Tan, "Machine Learning in Wireless Sensor Networks: Algorithms, Strategies, and Applications," in IEEE Communications Surveys & Tutorials, vol. 16, No. 4, pp. 1996-2018, Fourthquarter 2014, doi: 10.1109/COMST.2014. 2320099. (Year: 2014).*

M.-C. Huang, J. J. Liu, W. Xu, C. Gu, C. Li and M. Sarrafzadeh, "A Self-Calibrating Radar Sensor System for Measuring Vital Signs," in IEEE Transactions on Biomedical Circuits and Systems, vol. 10, No. 2, pp. 352-363, Apr. 2016, doi: 10.1109/TBCAS.2015.2411732. (Year: 2016).*

S. S. Ram and H. Ling, "Human motion animation using microDoppler signatures from multiple Doppler sensors," 2009 IEEE Antennas and Propagation Society International Symposium, North Charleston, SC, USA, 2009, pp. 1-4, doi: 10.1109/APS.2009.5171847 (Year: 2009).*

Singh et al., "A Real Time Patient Monitoring System based on Artificial Neural Fuzzy Inference System (ANFIS)", International Journal of Computer Applications, vol. 146, No. 15, Jul. 2016, pp. 22-28.

"Radar", Wikipedia, Retrieved on Nov. 25, 2019, Webpage available at : https://en.wikipedia.org/wiki/Radar.

Extended European Search Report received for corresponding European Patent Application No. 17182239.8, dated Jan. 29, 2018, 8 pages.

Kim et al., "Tracking a Moving Target with Multiple Doppler Sensors Using an Artificial Neural Network", IEEE Antennas and Propagation Society International Symposium, Jun. 9-15, 2007, pp. 1477-1480.

Ram et al., "Human Motion Animation Using MicroDoppler Signatures from Multiple Doppler Sensors", IEEE Antennas and Propagation Society International Symposium, Jun. 1-5, 2009, 4 pages.

Huang et al., "A Self-Calibrating Radar Sensor System for Measuring Vital Signs", IEEE Transactions on Biomedical Circuits and Systems, vol. 10, No. 2, Apr. 2016, pp. 352-363.

International Search Report and Written Opinion received for corresponding Patent Cooperation Treaty Application No. PCT/IB2018/055202, dated Oct. 9, 2018, 14 pages.

Office action received for corresponding European Patent Application No. 17182239.8, dated Apr. 20, 2020, 7 pages.

* cited by examiner

RF BASED MONITORING OF USER ACTIVITY

RELATED APPLICATION

This application was originally filed as Patent Cooperation Treaty Application No. PCT/IB2018/055202 filed Jul. 13, 2018 which claims priority benefit to European Patent Application No. 17182239.8, filed Jul. 20, 2017.

FIELD

The subject matter described herein relates to health and fitness monitors.

BACKGROUND

For many, the health benefits of being active, rather than sedentary, are clear. As such, it may not be too much of a surprise that body-worn health and fitness trackers have become increasingly popular to measure, sense, and/or track health related measurements of the wearer. For example, a health and fitness activity tracker, such as a body worn device or wearable, may be used to determine how many steps the wearer has taken over a given period of time, how many stairs the wearer has climbed over a given period of time, how high the user has jumped over a given period of time, how active is the wearer is over a given period of time, how many calories the user is expending, and/or the like.

SUMMARY

Methods and apparatus, including computer program products, are provided for activity tracking.

Methods and apparatus, including computer program products, are provided for activity tracking. In some example embodiments, there may be provided a method that includes deriving, from radio frequency based data, pseudo sensor data representative of at least an activity of a user, the pseudo sensor data derived based on at least a machine learning model configured to transform the radio frequency based data into the pseudo sensor data; and providing the pseudo sensor data.

In some variations, one or more of the features disclosed herein including the following features can optionally be included in any feasible combination. The radio frequency based data may be generated from radio frequency signals reflected from at least the user. The pseudo sensor data may represent data derived from the radio frequency based data, rather than data obtained directly from a sensor that generates native sensor data indicative of the activity of the user. The sensor may be coupled to, and/or included in, a user equipment associated with the user, wherein the sensor and/or the user equipment is worn by the user or not worn by the user. The pseudo sensor data may be provided to an application to enable the application to process the pseudo sensor data and the native sensor data to enable tracking the activity of the user. The pseudo sensor data and the native sensor data may provide a stream of data to the application to enable tracking the activity of the user. The pseudo sensor data may be derived in response to at least one gap in the native. The at least one gap may be caused at least in part by the sensor not being able to generate the native sensor data representative of the activity of the user. The sensor may not able to generate the native sensor data, when the sensor is not worn by the user and/or the user equipment is being charged. The pseudo sensor data may be derived in response to an indication that the user equipment and/or the sensor is not providing native sensor data for the user. The application may include a health and fitness tracker application. The user equipment may include a health and fitness tracker. The machine learning model may include a neural network, a linear regression model, a regression neural network, and/or a regression learning technique. The machine learning model may be configured by machine learning based on at least reference radio frequency based data and reference sensor data collected from at least one reference user performing activities comprising walking, running, jumping, gesturing, standing, and/or sitting. The native sensor data may include accelerometer data, gyroscope data, and/or barometer data. The pseudo sensor data may include pseudo accelerometer data, pseudo gyroscope data, and/or pseudo barometer data. The radio frequency based data may be generated from radar signals reflected from at least the user.

In some example embodiments, there may be provided an apparatus comprising means for deriving, from radio frequency based data, pseudo sensor data representative of at least an activity of a user, the pseudo sensor data derived based on at least a machine learning model configured to transform the radio frequency based data into the pseudo sensor data; and means for providing the pseudo sensor data.

The above-noted aspects and features may be implemented in systems, apparatus, methods, and/or articles depending on the desired configuration. The details of one or more variations of the subject matter described herein are set forth in the accompanying drawings and the description below. Features and advantages of the subject matter described herein will be apparent from the description and drawings, and from the claims.

Figure 1:
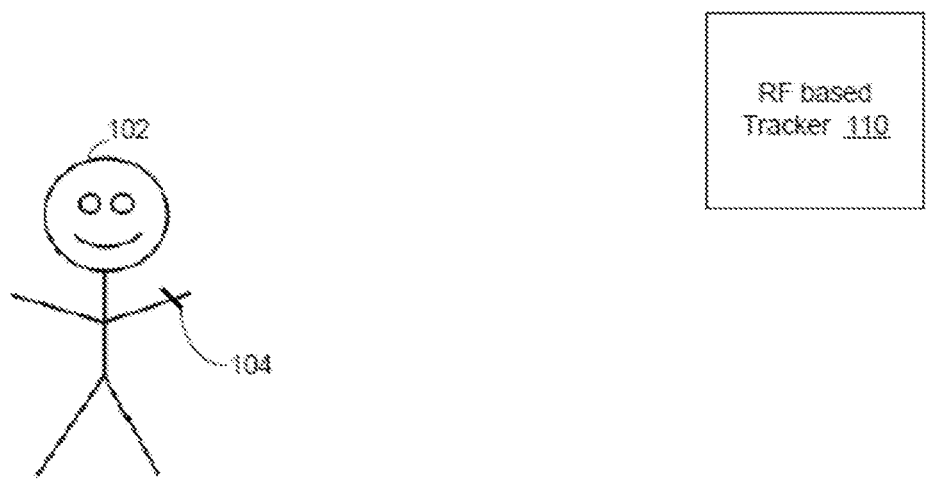
FIG. 1 depicts an example of a system including a radio frequency based tracker, in accordance with some example embodiments.

Like labels are used to refer to same or similar items in the drawings.

DETAILED DESCRIPTION

In the case of health and fitness trackers, some users have become very reliant on these trackers, so much so that some user's monitor their activity almost around the clock. However, the health and fitness tracker may, from time to time, not be useable for activity tracking. For example, the health and fitness tracker may not be providing data indicative of a user's activity due to a dead battery, communication link loss, removal from the user's body of the health and fitness tracker, and/or for other reasons. During the time the health and fitness tracker is not providing data indicative of a user's activity, the user's activity may not be tracked, which may be problematic for some users.

In some example embodiments, there is provided a radio frequency based tracker to track a user while, for example, the health and fitness tracker is not providing data indicative of a user's activity. For example, the health and fitness tracker may include, or be coupled to, at least one sensor that monitors a user's activity, such as walking, running, and/or other types of activity. But when the sensor is no longer able to provide data representative of the user's activity due to, for example, the health and fitness tracker and/or the sensor being removed from the user's body and/or for other reasons, the radio frequency (RE) based tracker may be used to track the user's activity, in accordance with some example embodiments.

In some example embodiments, the RF based tracker may transmit one or more radio frequency signals, and may receive the reflected returns resulting from the transmissions to enable tracking of the user's activity. In some example embodiments, the RF based tracker may include a radar to track the user's activity. In some example embodiments, the radar may be implemented as an ultra-wideband (UWB) radar, although other types of radios and/or radars may be used as well.

In some example embodiments, the RF based tracker may track the user's activity using RF signals, such as UWB signals or other types of signals, received as returns from the user being tracked. For example, the RF based tracker including the UWB radar may transmit UWB signals and then may receive UWB signals as they reflect back from the user. These UWB signals may carry or provide information that can be used to determine the location or distance of the user (including portions, such as body parts) with high-resolution over time. To illustrate further, the received RF signals, such as the UWB signals, may be detected and/or digitized to form RF based data, and this RF based data may be may be binned based on time of arrival to determine the location and/or position (and thus activity) of the user over time. In this way, the received RF signals (or RF based data representative of the RF signals) essentially paint a picture of the user's activity over time. However, this RF based data may not be readily processed by health and fitness tracker applications having application programming interfaces (APIs) accustomed to operating with, for example, sensor data, such as x-y-z accelerometer data or other types of sensor data, indicative of the user's activity.

In some example embodiments, the RF based data indicative of the user's activity over time may be transformed into pseudo sensor data, such as pseudo accelerometer data or other types of pseudo sensor data. The pseudo sensor data may be considered pseudo in the sense that the pseudo sensor data is derived from the RF based data. As noted above, sensors, such as accelerometers and/or the like, may natively generate sensor data that can be provided to an application, such as a health and fitness tracker application, to enable tracking the user's activity. Unlike the native sensor data that is generated directly by a sensor, the pseudo sensor data is derived from RF based data provided by RF based tracker disclosed herein. However, the form of the pseudo sensor data is similar to the native sensor data, such as that the pseudo sensor data can be readily processed by, for example, the health and fitness tracker application having an API accustomed to operating with native sensor data.

In some example embodiments, the RF based tracker may include a machine learning (ML) model that is trained, or configured to, transform the RF based data indicative of the user's activity into pseudo sensor data, such pseudo accelerometer data and/or other types of sensor data, which may be representative of the user's activity.

FIG. 1 depicts an example of a system 100, in accordance with some example embodiments.

In the example of FIG. 1, a health and fitness tracker 104 is being worn by a user 102. As the user performs an activity, such as walking, jumping, running, waving, gesturing, moving a body part (for example, moving one or both arms), and/or any other activity, the health and fitness tracker 104 may generate sensor data (also referred to herein as "native sensor data"). This native sensor data may be generated by at least one sensor associated with, or located at, the health and fitness tracker 104. For example, a sensor may comprise an accelerometer that generates sensor data, such as accelerometer data in the x, y, and z axis. This sensor data may be representative of (e.g., indicative of, or provide a measurement of, etc.) the user's activity (or lack of activity) such as running, jumping, walking, gesturing, and/or other activities performed by the user. Alternatively or additionally, the sensor may comprise a transducer, a pressure transducer, and/or a gyroscope, which may be indicative of the user's activity. Alternatively or additionally, the sensor may comprise a barometer, which may also indicate the user's activity (for example, change in elevation due to jumping or climbing).

As used herein, the health and fitness tracker (which may include, or be coupled, via wired and/or wireless connection(s), to at least one sensor such as an accelerometer and/or the like) may measure, generate, collect, and/or monitor one or more parameters associated with the activity of a user, such as miles walked, stairs climbed, calories burned, heart rate, breathing rate, and/or other activities associated with the user. In some example embodiments, a user equipment, such as the health and fitness tracker and/or the at least one sensor, may be worn by a user. For example, the health and fitness tracker and/or the at least one sensor may be implemented as a smartwatch, a user equipment, and/or other type of device or wearable. In some example embodiments however, the user equipment, such as the health and fitness tracker and/or the at least one sensor, may not be a wearable device worn by a user. For example, the health and fitness tracker and/or the at least one sensor may be implemented in a sheet, a pillow, and/or in other ways so as not to be considered a wearable.

To illustrate further, the health and fitness tracker 104 may correspond to a smartwatch, for example. An example of a health and fitness tracker is the Nokia Steel HR, which tracks a user's activity, although other types of health and fitness trackers may be used as well. The smartwatch may include a sensor that generates the sensor data natively. The native sensor data may be processed by an application or service, such as a health and fitness tracker application, at the smartwatch or at another device that is coupled (via a wireless or wired connection(s)) to the smartwatch. The other device may include a smartphone, a cloud server, and/or other types of user equipment and/or processors. Alternatively or additionally, the sensor may be a standalone sensor. For example, user 102 may wear or carry at least one sensor, such as an accelerometer, a barometer, and/or the like. The sensors may provide the sensor data to another device, such as a user equipment (for example, a smartwatch, a smart phone, and/or the like) and/or a remote server (for example, a cloud server coupled to the Internet). In the case of the cloud server, the cloud server may provide the application or service, such as the health and fitness tracker application providing activity tracking and other services.

Figure 2:
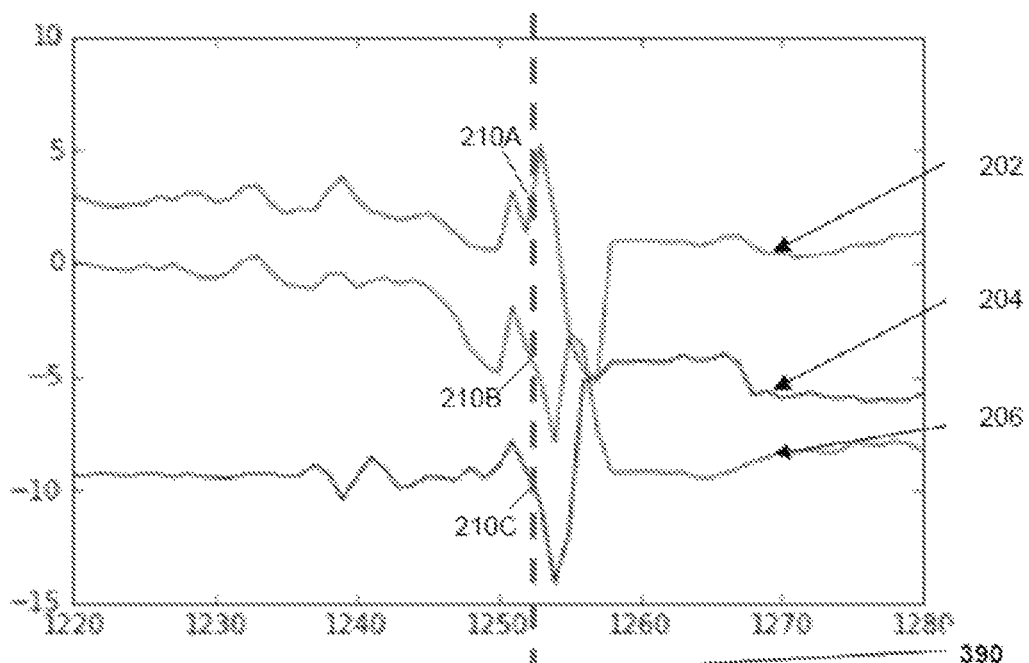
FIG. 2 depicts an example of a plot of sensor data such as accelerometer data, in accordance with some example embodiments.

FIG. 2 shows an example of sensor data, such as accelerometer data over time for the x-axis 202, y-axis 204, and z-axis 206, in accordance with some example embodiments. In the example of FIG. 2, the sensor may be coupled to, and/or included in, a user equipment such as the health and fitness tracker 104 (or a sensor) associated with the user. For example, the activity of the user may cause the health and fitness tracker 104 (or the associated sensor) to generate sensor data, from which the user's activity (e.g., steps walked, stairs climbed, miles run, calories burned, and/or other types of activity) can be determined.

Referring to FIGS. 1 and 2, the health and fitness tracker and/or associated sensor may natively generate sensor data, which in this example is x, y, and z accelerometer data, representative of the user's activity. This native sensor data may be provided to an application, such as a health and fitness tracker application or the application's API, to determine, as noted, the user's activity such as steps walked, stairs climbed, miles run, calories burned, and/or other types of activity. This application may located at the health and fitness tracker 104 and/or located at another device such as a remote device, an Internet coupled cloud server, a user equipment (for example, a smartphone), and/or the like.

The user 102 may, as noted, remove the health and fitness tracker 104 (and/or remove the sensor). When this is the case, the RF based tracker 110 (which may include one or more radios such as one or more UWB radars, for example) may track the user's 102 activity. For example, the user may be in a room, and as the user walks around the room, the RF based tracker may receive RF signal returns from the user. The received RF signals may be decoded and/or digitized into RF based data. From the RF based data, the pseudo sensor data may be derived using a machine learning model, in accordance with some example embodiments. Although the previous example illustrates native sensor data not being generated due to the removal of the health and fitness tracker 104 (and/or the associated sensor), the native sensor data may not be generated, as noted, for other reasons.

Figure 3A:
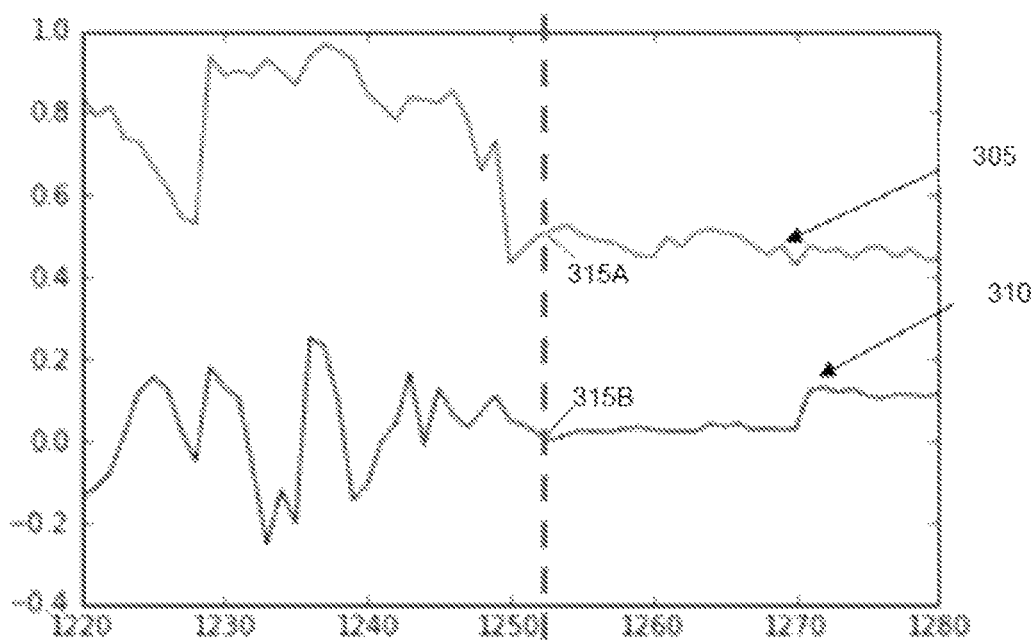
FIG. 3A depicts an example of plots of radio frequency based data, in accordance with some example embodiments.

FIG. 3A depicts an example of RF based data 305 and 310 received at the RF based tracker 110 in response to transmitted RF signals directed toward the user 102, in accordance with some example embodiments. In the example of FIG. 3A, the vertical line 390 represents a point in time during which the user 102 performs an activity. As shown at 390, the sensor data 202, 204, 206 indicates the activity at 210A-C, which corresponds in time to the RF based data activity 315A-B.

In the example of FIG. 3A, the RF based data is obtained from the UWB radar signals. However, other types of RF based signals may be used as well to provide RF based data representative of the user's position and/or location as a way to assess the user's activity. For example, other types of RF signals in accordance with WiFi, Bluetooth, millimeter wave (MMW), and/or other types of RF signals may be transmitted and/or received. From the received signals, RF based data may be generated representative of the user's activity. This RF based data may then be processed, as noted herein, to form pseudo sensor data, in accordance with some example embodiments.

In the case of an UWB radar, the UWB radar may, when compared to other types of radars, have a light power spectrum and transmit pulses having very short durations (for example, less than 1 nanosecond). The low power of UWB may enable safe use with human subjects, when compared to higher-powered radars.

In the case of the RF based data at FIG. 3A, this RF based data may, as noted, be transformed into pseudo sensor data, such as pseudo accelerometer data, in accordance with some example embodiments. In addition, this transformation may, as noted, be performed by a machine learning (ML) model trained, or configured, to transform the RF based data returned from the user, such as user 102, into the pseudo sensor data, in accordance with some example embodiments.

Although some of the examples refer to the sensor data as accelerometer data, the sensor data may take other forms as noted above, in which case the RF based tracker 110 may include a machine learning model configured to transform the RF based data to the other forms of pseudo sensor data.

Figure 3B:
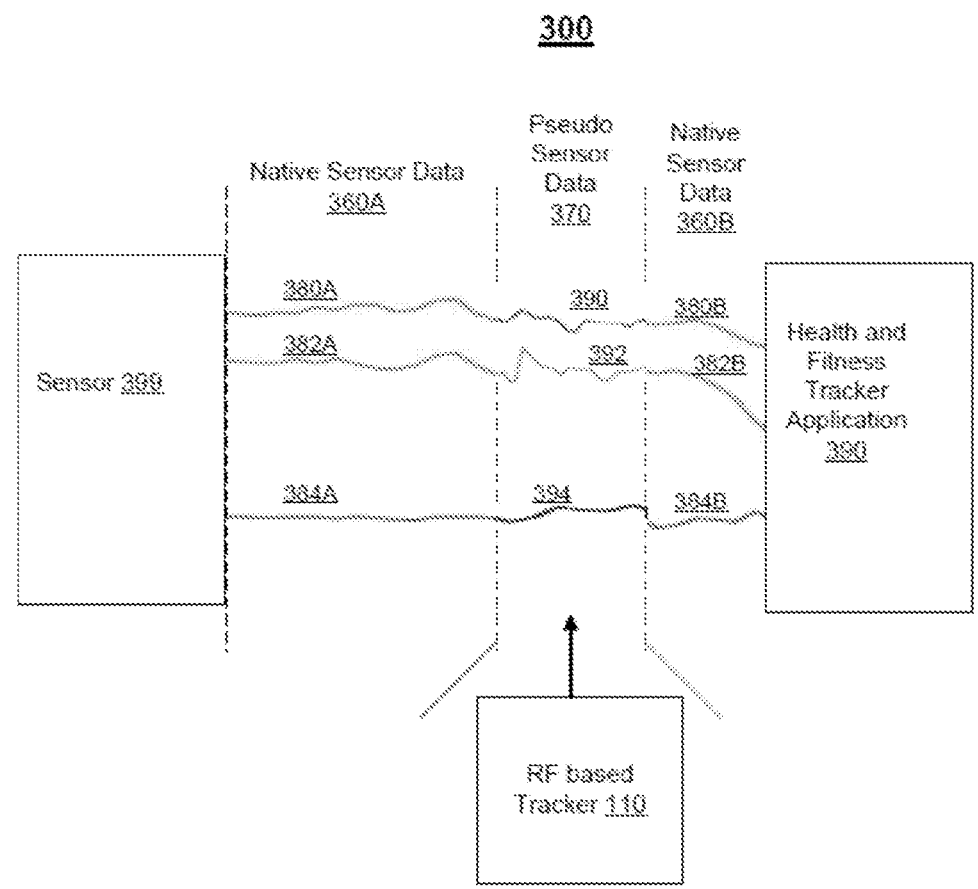
FIG. 3B depicts plots of native sensor data and pseudo sensor data being provided to an application or service, in accordance with some example embodiments.

FIG. 3B depicts an example of a system 300 including the health and fitness tracker 104 including a sensor 399, such as an accelerometer and/or other type of sensor, generating native sensor data 380A-B, 382A-B, and 384A-B while the health and fitness tracker 104 including the sensor is being worn 360A-B by user 102, in accordance with some example embodiments. However, when the health and fitness tracker 104 including the sensor 399 is not being worn (and thus not able to provide sensor data indicative or representative of the user's activity), the RF based tracker 110 may provide at 370 pseudo sensor data 390, 392, 394, in accordance with some example embodiments.

As can be seen from FIG. 3B, the pseudo sensor data may fill in at least a portion of the gap at 370 in the native sensor data to enable a more continuous (or nearly continuous) data stream representative of the user's activity. Specifically, the native sensor data in the form of, for example, accelerometer data 380A-B, 382A-B, and 384A-B along with the pseudo sensor data 390, 392, and 394 may be provided to an application 390, such as a health and fitness tracker application, to enable tracking the user's activity. The application 390 may, as noted above, be located at the health and fitness tracker 104 and/or located at another device such as a remote device, an Internet coupled cloud server, a user equipment (for example, a smartphone, smartwatch, or tablet), and/or the like.

To illustrate further, as a user is walking or performing some other activity for example, the health and fitness tracker 104 including the sensor 399 may generate the native sensor data 380A-B, 382A-B, and 384A-B, which contains information from which the user's activity can be determined. For example, the application 390 may determine the quantity of steps walked by the user over time from native sensor data 380A, 382A, and 384A, which in this example is accelerometer data indicative of steps walked over time. Even when the native sensor data is not available, the application 390 can determine the steps walked using the pseudo sensor data 390, 392, and 394. When the native sensor data is available again, the application may determine the steps walked from the remaining stream of native sensor data 380B, 382B, and 384B. In this way, the user's activity (which in this example corresponds to steps walked by the user) can be determined in a more continuous manner using native sensor data and pseudo sensor data, when compared to not using the pseudo sensor data in accordance with some example embodiments.

The "stream" of native sensor data, such as 380A, 382A, and 384B, may be considered continuous in the sense that the sensor 399 provides the native sensor data from time to time, such as at intervals of 0.25 second, 0.5 second, 1 second, 2 seconds, 30 seconds, 1 minute, and/or the like. For example, the sensor 399 may generate sensor data at these intervals, and this sensor data may still be considered continuous. However, if there is a time during which the sensor 399 cannot generate sensor data (e.g., due to charging or for other reasons as noted), this time may be considered a gap in the continuous stream of sensor data. In some embodiments, the gap may be defined by a predefined time where there is no sensor data, such as 2 minutes (although other times may be used as well), while in some embodiments, the gap may be defined by a message or trigger signal indicating that the sensor 399 is not able to generate sensor data.

Figure 4:
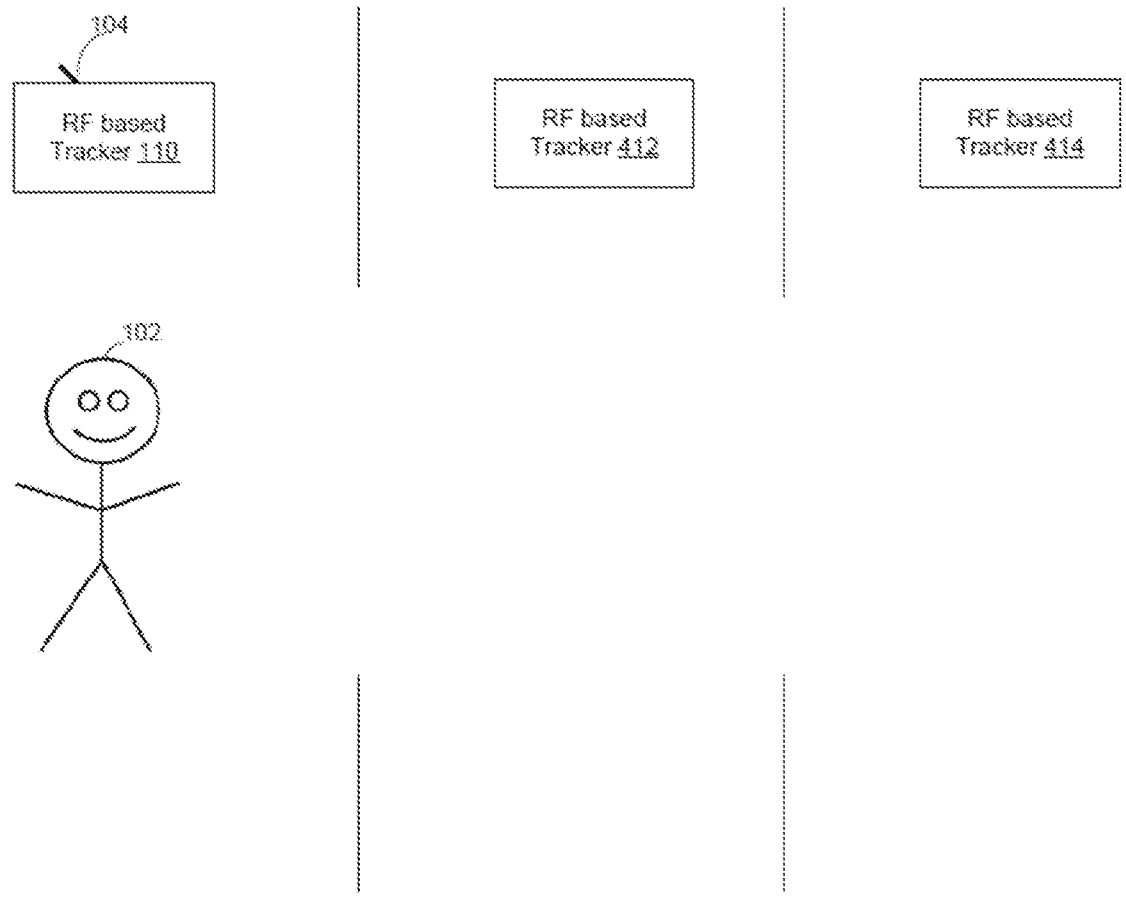
FIG. 4 depicts another example of a system including a radio-based tracker, in accordance with some example embodiments.

FIG. 4 depicts another example of a system 400, in accordance with some example embodiments. Unlike system 100, system 400 shows that the user 102 has docked the health and fitness tracker 104 (or sensor coupled to, or included in the tracker 104) at the RF based tracker 110 for charging or for some other reason.

FIG. 4 depicts that the RF based tracker 110 may operate cooperatively with other RF based trackers 412 and 414. For example, as the user 102 walks into a different room or building, the other the RF based tracker 412/414 may cooperatively generate and gather RF based data for the user 102. This collected RF based data may be processed by the RF based trackers 110, 410, and/or 412 to derive the pseudo sensor data, in accordance with some example embodiments. Alternatively or additionally, this collected RF based data may be forwarded to one of the RF based trackers 110, 410, and/or 412 for processing into the pseudo sensor data such as pseudo accelerometer data, in accordance with some example embodiments. Alternatively or additionally, the RF based data collected by one of more of the RF based trackers 110, 410, and/or 412 may be forwarded to another processor, such as a cloud server, a smart phone, and/or another processor-based device, to transform the RF based data into the pseudo sensor data, in accordance with some example embodiments.

In some example embodiments, the machine learning model may be trained, or configured, in a training phase. During the training phase, the RF based tracker 110 may collect reference RF based data from a user, such as a reference wearer. This reference wearer may be wearing the health and fitness tracker 104 and/or a sensor such as sensor 399, which generate reference sensor data, such as reference accelerometer data. For example, the reference wearer may perform one or more activities, such as sitting, walking, jumping, running, hand waving, and/or other types of activities. From this activity, the reference RF based data and the reference sensor data may be collected and then provided to a machine learning model. As used herein, the machine learning model refers to a transform, which may be configured or learned. Examples of machine learning models include a neural network, a linear regression model, a regression neural network, a regression technique, and/or other types of artificial intelligence technologies configured to learn how to transform time sequences of RF based data corresponding to the reference wearer's activity to pseudo sensor data, such as pseudo x-y-z accelerometer data or other types of pseudo sensor data. The learning may be performed in a supervised way and/or an unsupervised manner. Although the previous example reference to a reference wearer, the reference sensor data and reference RF based data may be collected from a plurality of references wearers as well.

Figure 5A:
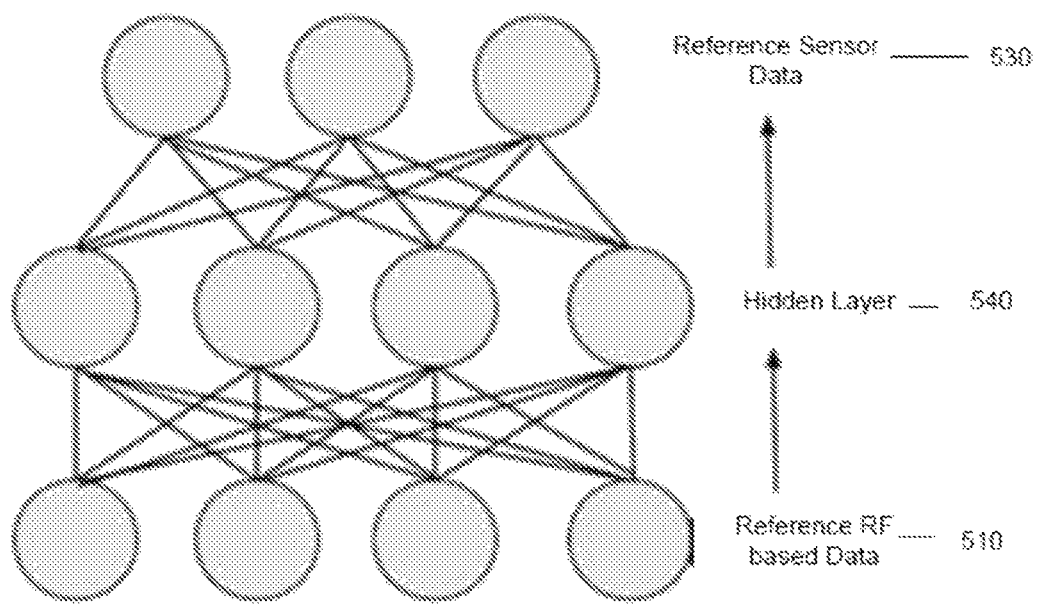
FIGS. 5A-5B depict examples of machine learning models, in accordance with some example embodiments.

FIG. 5A depicts an example of a machine learning model 599 in a training phase, in accordance with some example embodiments. As noted, the reference RF based data 510 may be provided at the input to the machine learning model, and reference sensor data 530 may be provided at the output. The machine learning model 599 (which in this example comprises a neural network) may include one or more layers, such as hidden layer(s) 540 configured to learn a configuration that provides the output 530 given the input 510. For example, the machine learning model 599 may iterate through the reference RF based data input 510 given the reference sensor data at the output until model 599 learns a hidden layer 540 configuration (e.g., a set of weights and/or other parameters).

To illustrate further, the machine learning model 599 may be implemented as a neural network including one or multi-layer perceptrons, such as multi-layer perceptron regressors. The one or more multi-layer perceptrons may learn by optimizing the squared loss (e.g., the square of the difference between 510 and 530) using gradient descent, such as a stochastic gradient descent, limited memory Broyden-Fletcher-Goldfarb-Shanno (LMBFGS), and/or the like. The multi-layer perceptron regressor may train iteratively through the reference data at the input 510 and output 530 since at each time step, the partial derivatives of the noted loss function (with respect to the model parameters) are computed to update the perceptron's parameters. Once the parameters of the machine learning model are learned, the trained machine learning model can be used generally for operational use to derive pseudo accelerometer data from RF based data.

Figure 5B:
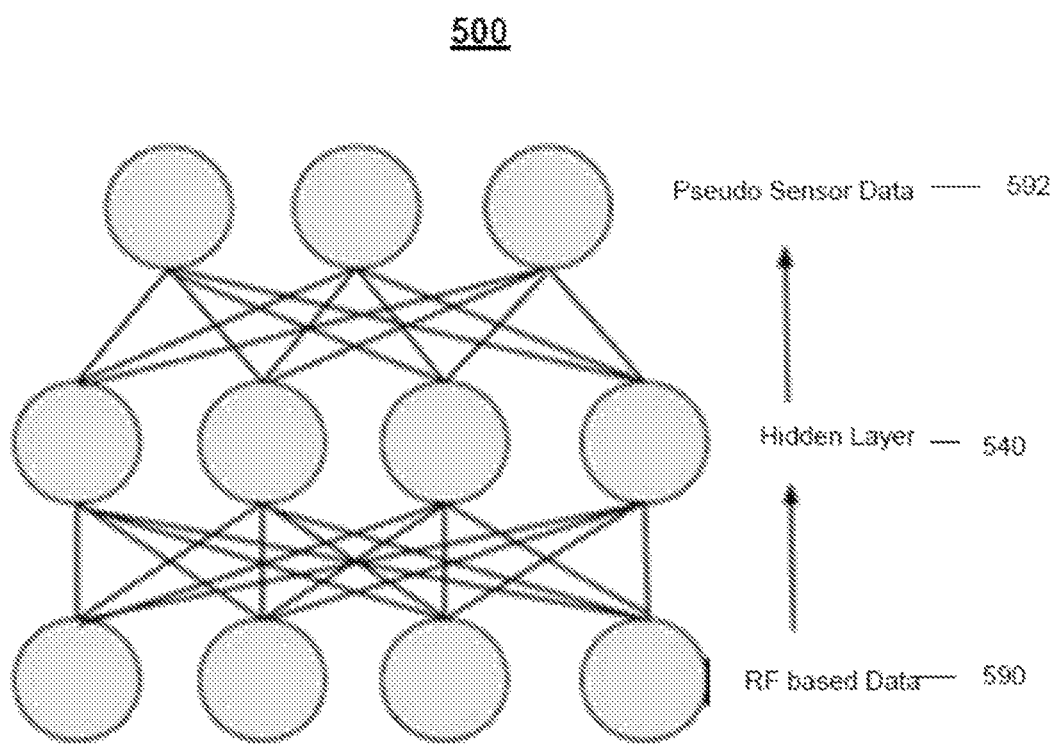

FIG. 5B depicts an example of a machine learning model 500 trained, or configured, to take RF based data 590, and provide the pseudo sensor data 592, such as pseudo accelerometer data (or other types of pseudo sensor data), in accordance with some example embodiments. After the machine learning model is trained, the trained machine learning model may serve as a transform that can be used generally to derive pseudo sensor data, such as pseudo accelerometer data, from the radar data. This pseudo sensor data can fill in at least a portion of any gaps, which may correspond to, for example, times that the tracker 104 and/or sensor 399 are not providing native sensor data. During these times, the RF based tracker 110 including the machine learning model 500 may receive as an input the native RF based data 590, and output pseudo sensor data 592, such as pseudo accelerometer data. In this way, the pseudo sensor data can fill in at least a portion of a gap (as shown at FIG. 3B at 370, for example) to enable providing a more continuous, or nearly continuous, stream of data for health and fitness tracking by the application 390, the health and fitness tracker 104, and/or the like.

Figure 5C:
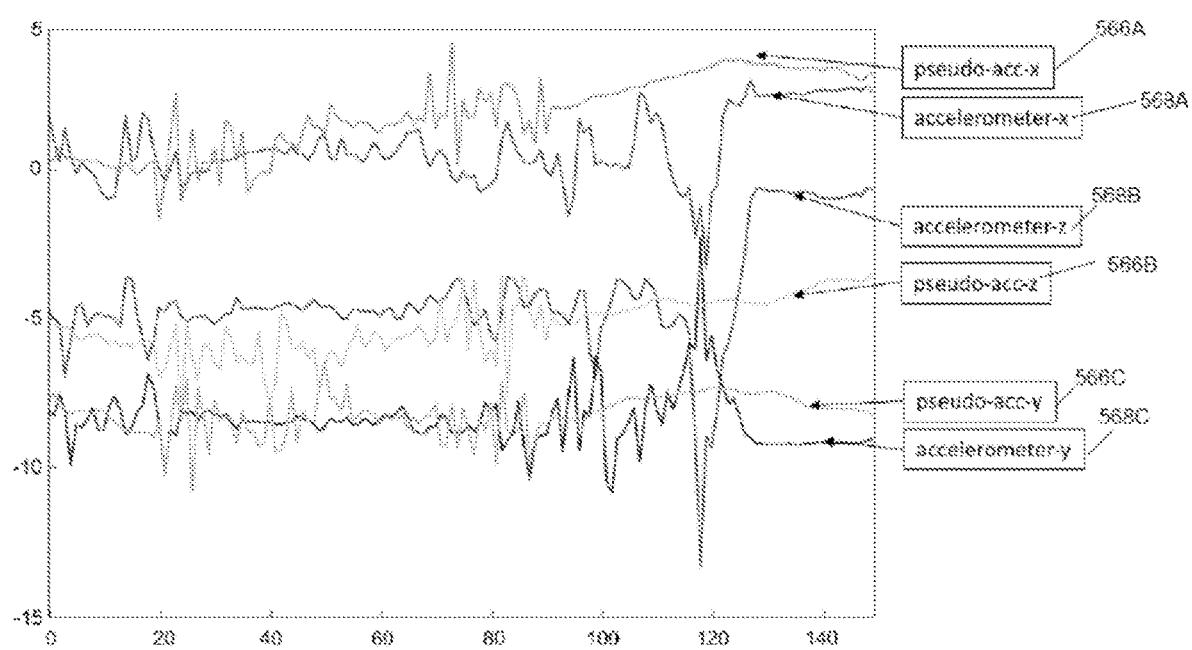
FIG. 5C depicts an example of plots of pseudo sensor data, in accordance with some example embodiments.

FIG. 5C plots native sensor data 568A-C and, for comparison, pseudo sensor data 566A-C, in accordance with some example embodiments. The pseudo sensor data 566A-C may be generated as noted using the trained, or configured, machine learning model 500. In the example of FIG. 5C, the pseudo sensor data 566A-C may be provided to a health and fitness tracker application, such as application 390 which may count steps or monitor and/or track other activity associated with a user. When this is the case, the health and fitness tracker application may yield a step count for example that is the same or similar to the step count obtained using native sensor data 568A-C.

Figure 6:
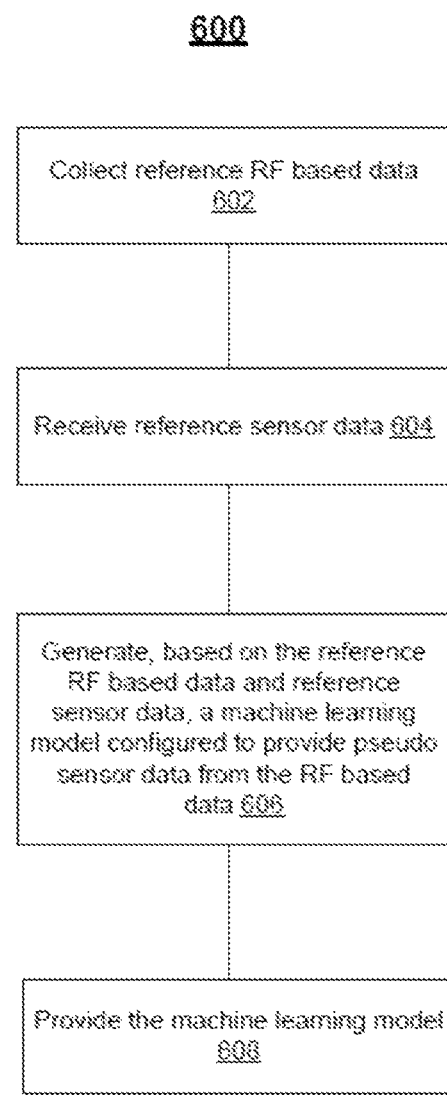
FIG. 6 depicts an example of a process for training a machine learning model to transform radio frequency based data into pseudo sensor data, in accordance with some example embodiments.

FIG. 6 depicts an example of a process 600 for generating a machine learning model during a training phase, in accordance with some example embodiments. The description of FIG. 6 also refers to FIGS. 1, 2, and 3.

At 602, the RF based tracker 110 may collect RF based reference data, in accordance with some example embodiments. For example, the RF based tracker 110 may, as noted, transmit RF signals, and then receive RF signals (which may be reflected, for example, back from a reference user 102). The received RF signals may be decoded and/or digitized, into RF based data, as noted above. Since the RF based data in this example is obtained from a reference user, the RF based data is referred as reference RF based data. As the reference user 102 is also wearing the health and fitness tracker 104 (and/or sensor 399, for example), the reference RF based data may correlate in time to sensor data, such as accelerometer data, natively generated by the health and fitness tracker 104 and/or sensor 399. Since the sensor data in this example is obtained from a reference user, this sensor data is referred as reference sensor data.

At 604, the RF based tracker 110 may receive, from the health and fitness tracker 104 (and/or sensor 399), the reference sensor data. Referring again to FIGS. 2 and 3A, if the user jumps or takes a step at time t1 (see, for example, 390), the reference RF based data at time t1 and the reference sensor data at time t1 correlate to the same activity, such as a jump or a step.

At 606, the radio frequency based tracker 110 may generate, based on the reference radar data and reference sensor data, a machine learning model, in accordance with some example embodiments. Referring also to the example at FIG. 5A, the machine learning model 599 may iterate through the reference RF based data input 510 given the reference sensor data at the output 530 until the model 599 learns a hidden layer 540 configuration (e.g., a set of weights and/or other parameters).

Once trained, the machine learning model may be provided, at 608, to the RF based tracker 110 for operational use, in accordance with some example embodiments. For example, the RF based tracker 110 may use the machine learning model (see, e.g., FIG. 5B at 500) to transform RF based data (which may be received when the wearer has taken off the activity tracker 104 or at other times native sensor data is not available or being generated) into pseudo sensor data, such as pseudo accelerometer data and/or other types of pseudo sensor data. This pseudo sensor data can be used, as noted, to fill in at least a portion of a gap in the user's native sensor data and thus provide a continuous, or nearly continuous, stream of data for activity tracking even when the native sensor data is not being generated or is not available (e.g., when the user is not wearing the activity tracker/sensor or for other reasons as noted).

Although some of the examples refer to a neural network, other types of machine learning models may be used as well.

Figure 7:
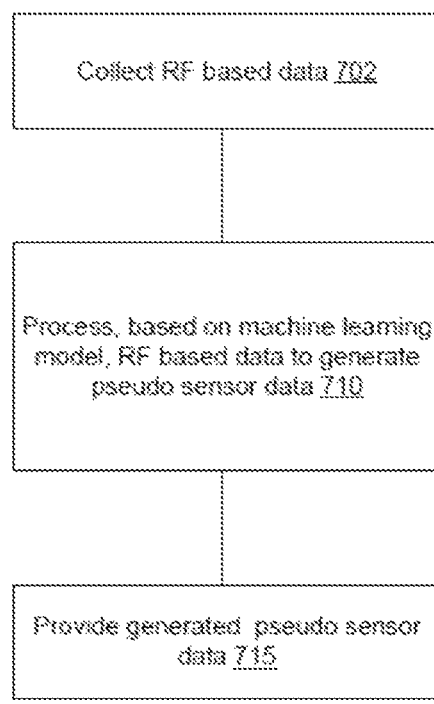
FIG. 7 depicts an example of a process for using the trained machine learning model in an operational phase to transform radio frequency based data into pseudo sensor data, in accordance with some example embodiments.

FIG. 7 depicts an example of a process 700 for the RF based tracker during an operational phase, in accordance with some example embodiments. The description of FIG. 7 also refers to FIGS. 1, 3B, and 5B.

At 702, the RF based tracker 110 may collect RF based data, in accordance with some example embodiments. For example, the health and fitness tracker 104 (or sensor 399 therein) may not be generating actual, native sensor data, such as accelerometer data, for a variety of reasons including the health and fitness tracker 104 and/or sensor 399 not being worn by user 102. When this is the case, the RF based tracker 110 may collect the RF based data for user 102 (an example of which is shown at FIG. 3A). The RF based data may correspond to decoded and/or detected returns, as noted above, from an RF signal transmitted towards the user 102. The RF signals sent towards or received from the user 102 may comprise a variety of types of radio frequency signals including UWB, WiFi, MMW, Bluetooth, and/or other types of signals. At 702, the health and fitness tracker 104 may, in accordance with some example embodiments, trigger the RF based tracker 110 to track the user 102 and initiate transmission and reception of RF signals. For example, the health and fitness tracker 104 may trigger the RF based tracker 110 to track the user 102 in response to the health and fitness tracker 104 (and/or sensor 399) being docked (for example, for charging) at the radio-based tracker 110. Alternatively or additionally, the health and fitness tracker 104 may trigger the RF based tracker 110 to track the user in response to the health and fitness tracker 104 transmitting an indication, such as by transmitting a trigger signal or sending a message, to the RF based tracker 110. Alternatively or additionally, the RF based tracker 110 may generate pseudo sensor data without a trigger or even when the health and fitness tracker (and/or sensor) is able to generate native sensor data.

At 710, the RF based tracker 110 may process the RF based data into pseudo sensor data such as pseudo accelerometer data and/or other types of pseudo sensor data, in accordance with some example embodiments. For example, the machine learning model 500 may derive (e.g., transform) the pseudo sensor data such as pseudo accelerometer data from the RF based data representative of the user's activity over time.

At 715, the pseudo sensor data such as the pseudo accelerometer data may be provided to an application 390 such as a health and fitness tracker application, in accordance with some example embodiments. For example, the RF-based tracker 110 (or other processor-based device) may provide the pseudo sensor data, via a wireless and/or wired interface, to the application 390 at a device, such as the health and fitness tracker 104 or other device. And, the application 390 may have an application programming interface configured to receive the pseudo sensor data (along with any native sensor data that may have been generated directly by the health and fitness tracker's 104 sensor), and to generate activity information, such as calories burned, steps walked, stairs climbed, miles walked, heart rate, breathing rate, and/or other types of activity to a user, such as user 102.

Figure 8:
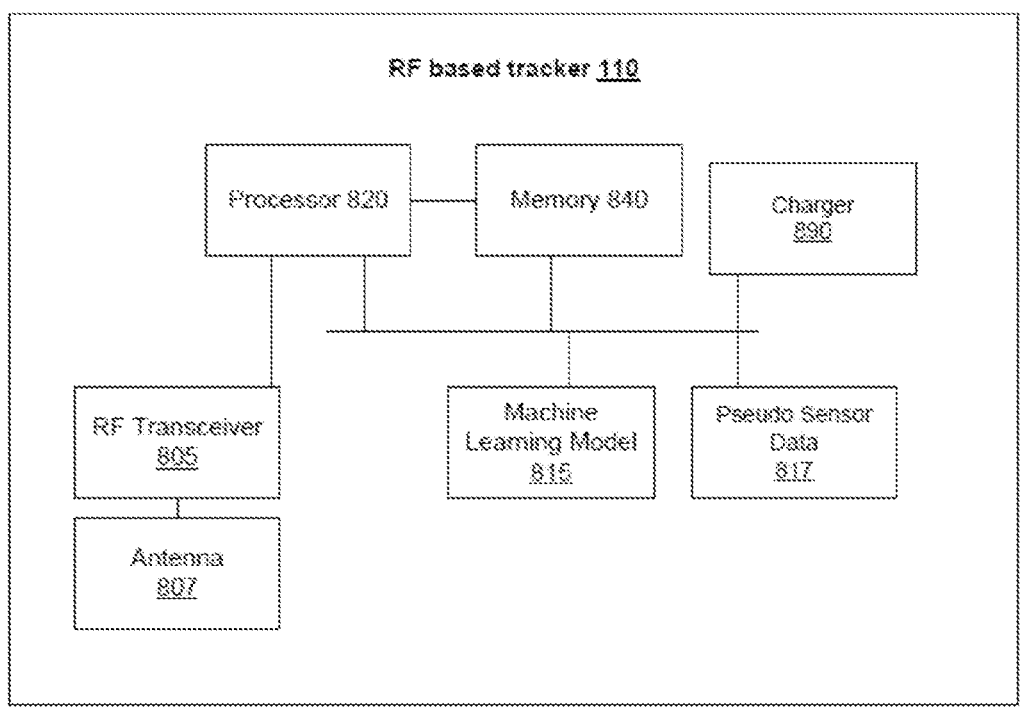
FIG. 8 depicts an example of a block diagram for a radio frequency based tracker, in accordance with some example embodiments.

FIG. 8 depicts an example of a RF based tracker 110, in accordance with some example embodiments. The RF based tracker 110 may include at least one processor 820 and at least one memory 840 including program code which when executed by the at least one processor 820 causes the operations disclosed herein with respect to the RF based tracker including, for example, deriving, from radio frequency based data, pseudo sensor data representative of at least an activity of a user, the pseudo sensor data derived based on at least a machine learning model configured to transform the radio frequency based data into the pseudo sensor data; and providing the pseudo sensor data. The RF based tracker 110 may include at least one antenna 807 coupled to an RF transceiver 805. The RF transceiver 805 may transmit and/or receive signals such as RF signals (e.g., radar signals and/or other types of RF signals), which can be used to enable tracking user 102. The RF transceiver and/or processor 820 may also control transmission and/or reception of the RF signals. Alternatively or additionally, the RF transceiver and/or processor 820 may generate (for example, decode and/or digitize) RF based data from received RF signals.

The RF-based tracker 110 may include a charger 890, which may be used to charge the activity tracker 104. In some example embodiments, when the activity tracker 104 is docked for charging (or for some other reason not able to provide native sensor data), the RF based tracker 110 may send RF signals, via RF transceiver 805 and antenna 807, to enable tracking the user's 102 activity. Furthermore, the RF-based tracker 110 may include a machine learning model 815, which can be used to derive pseudo sensor data 817 from RF based data.

Figure 9:
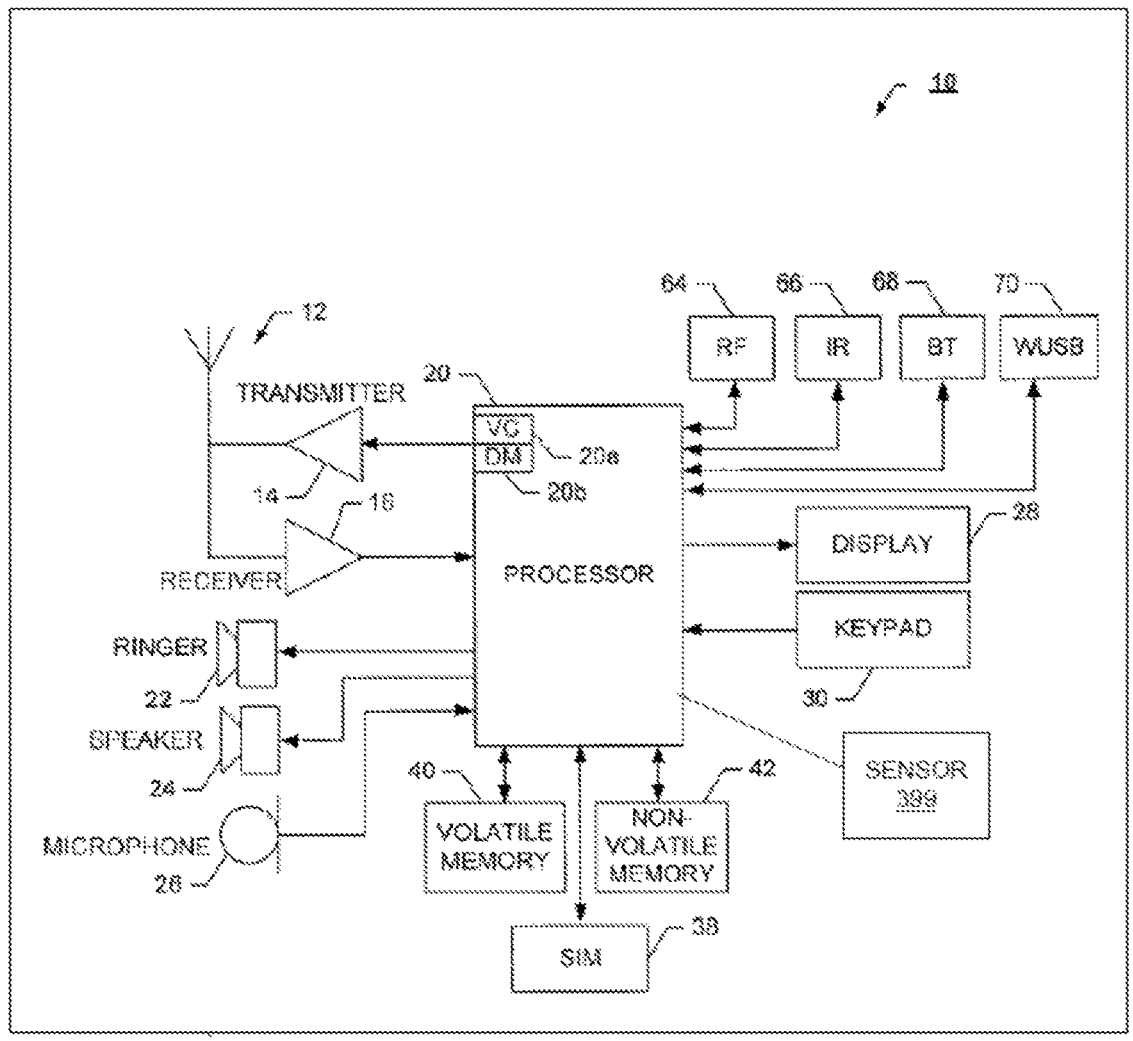
FIG. 9 depicts an example of an apparatus, in accordance with some example embodiments.

FIG. 9 illustrates a block diagram of an apparatus 10, in accordance with some example embodiments. The apparatus 10 may represent a user equipment, such as a smart phone and/or other processor based device, or may represent other type of wireless device which may serve as a standalone health and fitness tracker 104. For example, the apparatus may include at least one sensor 399, such as an accelerometer, a pressure transducer, a barometer, and/or the like. Alternatively or additionally, a sensor may couple to apparatus 10, which collectively provide the health and fitness tracker 104. As used herein, a health and fitness tracker refers to a device that at least monitors, measures, determines, tracks, and/or collects one or more parameters associated with a user's activity. Examples of these parameters include health and/or fitness related parameters, such as steps walked, stairs climbed, miles/kilometers walked, heart rate, breathing rate, calories burned, sleep patterns, weight management, and/or the like.

The apparatus 10 may include at least one antenna 12 in communication with a transmitter 14 and a receiver 16. Alternatively transmit and receive antennas may be separate. The apparatus 10 may also include a processor 20 configured to provide signals to and receive signals from the transmitter and receiver, respectively, and to control the functioning of the apparatus. Processor 20 may be configured to control the functioning of the transmitter and receiver by effecting control signaling via electrical leads to the transmitter and receiver. Likewise, processor 20 may be configured to control other elements of apparatus 10 by effecting control signaling via electrical leads connecting processor 20 to the other elements, such as a display or a memory. The processor 20 may, for example, be embodied in a variety of ways including circuitry, at least one processing core, one or more microprocessors with accompanying digital signal processor(s), one or more processor(s) without an accompanying digital signal processor, one or more coprocessors, one or more multi-core processors, one or more controllers, processing circuitry, one or more computers, various other processing elements including integrated circuits (for example, an application specific integrated circuit (ASIC), a field programmable gate array (FPGA), and/or the like), or some combination thereof. Accordingly, although illustrated in FIG. 9 as a single processor, in some example embodiments the processor 20 may comprise a plurality of processors or processing cores.

The apparatus 10 may be capable of operating with one or more air interface standards, communication protocols, modulation types, access types, and/or the like. Signals sent and received by the processor 20 may include signaling information in accordance with an air interface standard of an applicable cellular system, and/or any number of different wireline or wireless networking techniques, comprising but not limited to Wi-Fi, wireless local access network (WLAN) techniques, such as Institute of Electrical and Electronics Engineers (IEEE) 802.11, 802.16, 802.3, ADSL, DOCSIS, and/or the like. In addition, these signals may include speech data, user generated data, user requested data, and/or the like.

For example, the apparatus 10 and/or a cellular modem therein may be capable of operating in accordance with various first generation (1G) communication protocols, second generation (2G or 2.5G) communication protocols, third-generation (3G) communication protocols, fourth-generation (4G) communication protocols, fifth-generation (5G) communication protocols, Internet Protocol Multimedia Subsystem (IMS) communication protocols (for example, session initiation protocol (SIP) and/or the like. For example, the apparatus 10 may be capable of operating in accordance with 2G wireless communication protocols IS-136, Time Division Multiple Access TDMA, Global System for Mobile communications, GSM, IS-95, Code Division Multiple Access, CDMA, and/or the like. In addition, for example, the apparatus 10 may be capable of operating in accordance with 2.5G wireless communication protocols General Packet Radio Service (GPRS), Enhanced Data GSM Environment (EDGE), and/or the like. Further, for example, the apparatus 10 may be capable of operating in accordance with 3G wireless communication protocols, such as Universal Mobile Telecommunications System (UMTS), Code Division Multiple Access 2000 (CDMA2000), Wideband Code Division Multiple Access (WCDMA), Time Division-Synchronous Code Division Multiple Access (TD-SCDMA), and/or the like. The apparatus 10 may be additionally capable of operating in accordance with 3.9G wireless communication protocols, such as Long Term Evolution (LTE), Evolved Universal Terrestrial Radio Access Network (E-UTRAN), and/or the like. Additionally, for example, the apparatus 10 may be capable of operating in accordance with 4G wireless communication protocols, such as LTE Advanced, 5G, and/or the like as well as similar wireless communication protocols that may be subsequently developed.

It is understood that the processor 20 may include circuitry for implementing audio/video and logic functions of apparatus 10. For example, the processor 20 may comprise a digital signal processor device, a microprocessor device, an analog-to-digital converter, a digital-to-analog converter, and/or the like. Control and signal processing functions of the apparatus 10 may be allocated between these devices according to their respective capabilities. The processor 20 may additionally comprise an internal voice coder (VC) 20a, an internal data modem (DM) 20b, and/or the like. Further, the processor 20 may include functionality to operate one or more software programs, which may be stored in memory. In general, processor 20 and stored software instructions may be configured to cause apparatus 10 to perform actions. For example, processor 20 may be capable of operating a connectivity program, such as a web browser. The connectivity program may allow the apparatus 10 to transmit and receive web content, such as location-based content, according to a protocol, such as wireless application protocol, WAP, hypertext transfer protocol, HTTP, and/or the like.

Apparatus 10 may also comprise a user interface including, for example, an earphone or speaker 24, a ringer 22, a microphone 26, a display 28, a user input interface, and/or the like, which may be operationally coupled to the processor 20. The display 28 may, as noted above, include a touch sensitive display, where a user may touch and/or gesture to make selections, enter values, and/or the like. The processor 20 may also include user interface circuitry configured to control at least some functions of one or more elements of the user interface, such as the speaker 24, the ringer 22, the microphone 26, the display 28, and/or the like. The processor 20 and/or user interface circuitry comprising the processor 20 may be configured to control one or more functions of one or more elements of the user interface through computer program instructions, for example, software and/or firmware, stored on a memory accessible to the processor 20, for example, volatile memory 40, non-volatile memory 42, and/or the like. The apparatus 10 may include a battery for powering various circuits related to the mobile terminal, for example, a circuit to provide mechanical vibration as a detectable output. The user input interface may comprise devices allowing the apparatus 20 to receive data, such as a keypad 30 (which can be a virtual keyboard presented on display 28 or an externally coupled keyboard) and/or other input devices.

As shown in FIG. 9, apparatus 10 may also include one or more mechanisms for sharing and/or obtaining data. For example, the apparatus 10 may include a short-range radio frequency (RF) transceiver and/or interrogator 64, so data may be shared with and/or obtained from electronic devices in accordance with RF techniques. The apparatus 10 may include other short-range transceivers, such as an infrared (IR) transceiver 66, a Bluetooth™ (BT) transceiver 68 operating using Bluetooth™ wireless technology, a wireless universal serial bus (USB) transceiver 70, a Bluetooth™ Low Energy transceiver, a ZigBee transceiver, an ANT transceiver, a cellular device-to-device transceiver, a wireless local area link transceiver, and/or any other short-range radio technology. Apparatus 10 and, in particular, the short-range transceiver may be capable of transmitting data to and/or receiving data from electronic devices within the proximity of the apparatus, such as within 10 meters, for example. The apparatus 10 including the Wi-Fi or wireless local area networking modem may also be capable of transmitting and/or receiving data from electronic devices according to various wireless networking techniques, including 6LoWpan, Wi-Fi, Wi-Fi low power, WLAN techniques such as IEEE 802.11 techniques, IEEE 802.15 techniques, IEEE 802.16 techniques, and/or the like.

The apparatus 10 may comprise memory, such as a subscriber identity module (SIM) 38, a removable user identity module (R-UIM), an eUICC, an UICC, and/or the like, which may store information elements related to a mobile subscriber. In addition to the SIM, the apparatus 10 may include other removable and/or fixed memory. The apparatus 10 may include volatile memory 40 and/or non-volatile memory 42. For example, volatile memory 40 may include Random Access Memory (RAM) including dynamic and/or static RAM, on-chip or off-chip cache memory, and/or the like. Non-volatile memory 42, which may be embedded and/or removable, may include, for example, read-only memory, flash memory, magnetic storage devices, for example, hard disks, floppy disk drives, magnetic tape, optical disc drives and/or media, non-volatile random access memory (NVRAM), and/or the like. Like volatile memory 40, non-volatile memory 42 may include a cache area for temporary storage of data. At least part of the volatile and/or non-volatile memory may be embedded in processor 20. The memories may store one or more software programs, instructions, pieces of information, data, and/or the like which may be used by the apparatus for performing operations disclosed herein including, for example, deriving, from radio frequency based data, pseudo sensor data representative of at least an activity of a user, the pseudo sensor data derived based on at least a machine learning model configured to transform the radio frequency based data into the pseudo sensor data; and providing the pseudo sensor data.

The memories may comprise an identifier, such as an international mobile equipment identification (IMEI) code, capable of uniquely identifying apparatus 10. The memories may comprise an identifier, such as an international mobile equipment identification (IMEI) code, capable of uniquely identifying apparatus 10. In the example embodiment, the processor 20 may be configured using computer code stored at memory 40 and/or 42 to control and/or provide one or more aspects disclosed herein (see, for example, process 600, 700, and/or other operations disclosed herein). For example, the processor 20 may be configured using computer code stored at memory 40 and/or 42 to at least including, for example, deriving, from radio frequency based data, pseudo sensor data representative of at least an activity of a user, the pseudo sensor data derived based on at least a machine learning model configured to transform the radio frequency based data into the pseudo sensor data; and providing the pseudo sensor data. Moreover, the processor 20 may be configured using computer code stored at memory 40 and/or 42 to at least collect reference RF based data and reference sensor data from a reference wearer and then generate a machine learning model configured to derive pseudo accelerometer data from RF based data.

Some of the embodiments disclosed herein may be implemented in software, hardware, application logic, or a combination of software, hardware, and application logic. The software, application logic, and/or hardware may reside on memory 40, the control apparatus 20, or electronic components, for example. In some example embodiment, the application logic, software or an instruction set is maintained on any one of various conventional computer-readable media. In the context of this document, a "computer-readable medium" may be any non-transitory media that can contain, store, communicate, propagate or transport the instructions for use by or in connection with an instruction execution system, apparatus, or device, such as a computer or data processor circuitry, with examples depicted at FIG. 9, computer-readable medium may comprise a non-transitory computer-readable storage medium that may be any media that can contain or store the instructions for use by or in connection with an instruction execution system, apparatus, or device, such as a computer.

Without in any way limiting the scope, interpretation, or application of the claims appearing below, a technical effect of one or more of the example embodiments disclosed herein is enhanced tracking of a user or wearer's activity.

Although some of the examples refer to the activities in terms of walking, running, jumping, and/or the like. The user's activity may include body functions, such as heart rate, breathing rate, sleep patterns, weight management, and/or other functions. For example, an RF signal may be transmitted towards a user, and the reflected RF signals that are returned may be processed (e.g., binned, etc.) to determine breathing rate (which can be determined as a change in distance caused by the expanding chest cavity). Further, the RF signals may include information indicating heart rate, for example. As such, the activity in terms of breathing rate and/or heart rate may also be determined Moreover, although some of the examples refer to the pseudo sensor data being used in combination with native sensor data, the pseudo sensor data may be generated alone.

The subject matter described herein may be embodied in systems, apparatus, methods, and/or articles depending on the desired configuration. For example, the base stations and user equipment (or one or more components therein) and/or the processes described herein can be implemented using one or more of the following: a processor executing program code, an application-specific integrated circuit (ASIC), a digital signal processor (DSP), an embedded processor, a field programmable gate array (FPGA), and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device. These computer programs (also known as programs, software, software applications, applications, components, program code, or code) include machine instructions for a programmable processor, and may be implemented in a high-level procedural and/or object-oriented programming language, and/or in assembly/machine language. As used herein, the term "computer-readable medium" refers to any computer program product, machine-readable medium, computer-readable storage medium, apparatus and/or device (for example, magnetic discs, optical disks, memory, Programmable Logic Devices (PLDs)) used to provide machine instructions and/or data to a programmable processor, including a machine-readable medium that receives machine instructions. Similarly, systems are also described herein that may include a processor and a memory coupled to the processor. The memory may include one or more programs that cause the processor to perform one or more of the operations described herein.

Although a few variations have been described in detail above, other modifications or additions are possible. In particular, further features and/or variations may be provided in addition to those set forth herein. Moreover, the implementations described above may be directed to various combinations and subcombinations of the disclosed features and/or combinations and subcombinations of several further features disclosed above. Other embodiments may be within the scope of the following claims.

If desired, the different functions discussed herein may be performed in a different order and/or concurrently with each other. Furthermore, if desired, one or more of the above-described functions may be optional or may be combined. Although various aspects of some of the embodiments are set out in the independent claims, other aspects of some of the embodiments comprise other combinations of features from the described embodiments and/or the dependent claims with the features of the independent claims, and not solely the combinations explicitly set out in the claims. It is also noted herein that while the above describes example embodiments, these descriptions should not be viewed in a limiting sense. Rather, there are several variations and modifications that may be made without departing from the scope of some of the embodiments as defined in the appended claims. Other embodiments may be within the scope of the following claims. The term "based on" includes "based on at least." The use of the phase "such as" means "such as for example" unless otherwise indicated.

The invention claimed is:

1. A method comprising:
    deriving using a first apparatus comprising a radio frequency based tracker, from radio frequency based data, pseudo sensor data representative of at least an activity of a user, the pseudo sensor data derived based on at least a machine learning model configured to transform the radio frequency based data into the pseudo sensor data; and
    providing, using the first apparatus comprising the radio frequency based tracker, the pseudo sensor data derived from the radio frequency based data based on at least the machine learning model to a second apparatus comprising a health or fitness tracker application to enable the health or fitness tracker application to process the pseudo sensor data and native sensor data to enable tracking of the activity and health or fitness of the user, wherein the first apparatus is different from the second apparatus, and the first apparatus is configured to be separate from the second apparatus;
    wherein the pseudo sensor data is derived and provided to the second apparatus using the first apparatus comprising the radio frequency based tracker during a time interval when the native sensor data representative of the activity of the user that is associated with the second apparatus comprising the health or fitness tracker application is not provided, or when the native sensor data representative of the activity of the user is unavailable to the second apparatus comprising the health or fitness tracker application;
    wherein an amount of time between when the native sensor data representative of the activity of the user that is associated with the second apparatus comprising the health or fitness tracker application begins to not be provided to the second apparatus comprising the health or fitness tracker application or when the native sensor data representative of the activity of the user begins to be unavailable to the second apparatus comprising the health or fitness tracker application, and when the pseudo sensor data begins to be provided to the second apparatus comprising the health or fitness tracker application using the first apparatus comprising the radio frequency based tracker, is less than a threshold amount of time.

2. The method of claim 1, wherein the radio frequency based data is generated from radio frequency signals reflected from at least the user, wherein the health or fitness tracker application does not process the radio frequency based data.

3. The method of claim 2, wherein:
    the machine learning model comprises a neural network, a linear regression model, a regression neural network, or a regression learning technique, and wherein the machine learning model is configured with machine learning based on at least reference radio frequency based data and reference sensor data collected from at least one reference user performing activities comprising walking, running, jumping, gesturing, standing, or sitting, and wherein a user equipment comprises the health or fitness tracker application; and
    wherein the native sensor data comprises accelerometer data, gyroscope data, or barometer data, wherein the pseudo sensor data comprises pseudo accelerometer data, pseudo gyroscope data, or pseudo barometer data, and wherein the radio frequency based data is generated from radar signals reflected from at least the user.

4. The method of claim 2, wherein the pseudo sensor data is derived in response to at least one gap in the native sensor data, the at least one gap caused at least in part with a sensor, that generates the native sensor data representative of activity of the user, not being able to generate the native sensor data representative of the activity of the user.

5. The method of claim 1, wherein the pseudo sensor data represents data derived from the radio frequency based data, rather than data obtained directly from a sensor that generates the native sensor data indicative of the activity of the user.

6. The method of claim 5, wherein the sensor is coupled to, or included in, a user equipment associated with the user, wherein the sensor or the user equipment is worn by the user or not worn by the user.

7. The method of claim 5, wherein the pseudo sensor data is provided from the first apparatus that generates the pseudo sensor data using the machine learning model to the second apparatus comprising the health or fitness tracker application to process the pseudo sensor data and the native sensor data, the native sensor data generated with the second apparatus using the sensor.

8. The method of claim 5, wherein the pseudo sensor data and the native sensor data provide a stream of data to the health or fitness tracker application to enable the tracking of the activity of the user, or wherein the pseudo sensor data is derived in response to at least one gap in the native sensor data, the at least one gap caused at least in part with the sensor not being able to generate the native sensor data representative of the activity of the user.

9. The method of claim 5, wherein the pseudo sensor data is derived in response to an indication that the sensor is not providing the native sensor data for the user.

10. The method of claim 1, further comprising performing at least one or more of:
   docking, using the first apparatus, the second apparatus, wherein the first apparatus comprising the radio frequency based tracker provided the pseudo sensor data during the time interval when the first apparatus is docking the second apparatus, or
   charging, using the first apparatus, the second apparatus, wherein the first apparatus comprising the radio frequency based tracker provides the pseudo sensor data during the time interval when the first apparatus is charging the second apparatus.

11. The method of claim 1, wherein the machine learning model is trained with training data comprising at least reference radio frequency based data and reference sensor data, the reference radio frequency based data and the reference sensor data collected from at least one reference user performing at least one activity, wherein the machine learning model is trained using supervised training with the reference sensor data, and wherein the training comprises learning at least one relationship between the reference radio frequency based data obtained at points in time and the reference sensor data obtained at the respective points in time, wherein the training of the machine learning model with the reference radio frequency based data and the reference sensor data comprises learning at least one parameter used to derive the pseudo sensor data with the first apparatus from the radio frequency based data.

12. The method of claim 1, further comprising:
   sending, by the second apparatus comprising the health and fitness tracker application to the first apparatus comprising the radio frequency based tracker, a trigger message that indicates to the first apparatus comprising the radio frequency based tracker to begin providing the pseudo sensor data;
   wherein the trigger message that indicates to the first apparatus comprising the radio frequency based tracker to begin providing the pseudo sensor data that is sent by the second apparatus comprising the health and fitness tracker application is based on the threshold amount of time.

13. The method of claim 1, wherein the threshold amount of time comprises a gap in time when the native sensor data representative of the activity of the user that is associated with the second apparatus comprising the health or fitness tracker application is not provided, or when the native sensor data representative of the activity of the user is unavailable to the second apparatus comprising the health or fitness tracker application.

14. The method of claim 1, wherein the pseudo sensor data begins to be provided to the second apparatus comprising the health or fitness tracker application using the first apparatus comprising the radio frequency based tracker due to the native sensor data representative of the activity of the user that is associated with the second apparatus comprising the health or fitness tracker application not being provided to the second apparatus comprising the health or fitness tracker application or the native sensor data representative of the activity of the user being unavailable to the second apparatus comprising the health or fitness tracker application.

15. An apparatus comprising:
   at least one processor; and
   at least one memory storing instructions that, when executed by the at least one processor, cause the apparatus at least to:
   derive using the apparatus comprising a radio frequency based tracker, from radio frequency based data, pseudo sensor data representative of at least an activity of a user, the pseudo sensor data derived based on at least a machine learning model configured to transform the radio frequency based data into the pseudo sensor data; and
   provide, using the apparatus comprising the radio frequency based tracker, the pseudo sensor data derived from the radio frequency based data based on at least the machine learning model to another apparatus comprising a health or fitness tracker application to enable the health or fitness tracker application to process the pseudo sensor data and native sensor data to enable tracking of the activity and health or fitness of the user, wherein the apparatus is different from the another apparatus, and the apparatus is configured to be separate from the another apparatus;
   wherein the pseudo sensor data is derived and provided to the another apparatus using the apparatus comprising the radio frequency based tracker during a time interval when the native sensor data representative of the activity of the user that is associated with the second apparatus comprising the health or fitness tracker application is not provided, or when the native sensor data representative of the activity of the user is unavailable to the second apparatus comprising the health or fitness tracker application;
   wherein an amount of time between when the native sensor data representative of the activity of the user that is associated with the second apparatus comprising the health or fitness tracker application begins to not be provided to the second apparatus comprising the health or fitness tracker application or when the native sensor data representative of the activity of the user begins to be unavailable to the second apparatus comprising the health or fitness tracker application, and when the pseudo sensor data begins to be provided to the second apparatus comprising the health or fitness tracker application using the first apparatus comprising the radio frequency based tracker, is less than a threshold amount of time.

16. The apparatus of claim 15, wherein the radio frequency based data is generated from radio frequency signals reflected from at least the user.

17. The apparatus of claim 15, wherein the pseudo sensor data represents data derived from the radio frequency based data, rather than data obtained directly from a sensor that generates the native sensor data indicative of the activity of the user.

18. The apparatus of claim 17, wherein the sensor is coupled to, or included in, a user equipment associated with the user, wherein the sensor or the user equipment is worn by the user or not worn by the user.

19. The apparatus of claim 17, wherein the health or fitness tracker application does not process the radio frequency based data, and wherein a user equipment comprises the health or fitness tracker application.

20. The apparatus of claim 19, wherein the pseudo sensor data and the native sensor data provide a stream of data to the health or fitness tracker application to enable the tracking of the activity of the user, or wherein the pseudo sensor data is derived in response to at least one gap in the native sensor data, the at least one gap caused at least in part with the sensor not being able to generate the native sensor data representative of the activity of the user.

21. The apparatus of claim 20, wherein the sensor is not able to generate the native sensor data when the sensor is not worn by the user and the user equipment is being charged.

22. The apparatus of claim 15, wherein the instructions, when executed by the at least one processor, cause the apparatus at least to:
   receive, with the apparatus comprising the radio frequency based tracker from the another apparatus comprising the health or fitness tracker application, an indication to track the user; and
   provide, with the apparatus comprising the radio frequency based tracker to the another apparatus comprising the health or fitness tracker application, the pseudo sensor data in response to receiving, with the apparatus comprising the radio frequency based tracker from the another apparatus comprising the health or fitness tracker application, the indication to track the user.

23. A non-transitory computer readable medium comprising program instructions for causing a first apparatus to perform at least the following:

deriving using a first apparatus comprising a radio frequency based tracker, from radio frequency based data, pseudo sensor data representative of at least an activity of a user, the pseudo sensor data derived based on at least a machine learning model configured to transform the radio frequency based data into the pseudo sensor data; and providing, using the first apparatus comprising the radio frequency based tracker, the pseudo sensor data derived from the radio frequency based data based on at least the machine learning model to a second apparatus comprising a health or fitness tracker application to enable the health or fitness tracker application to process the pseudo sensor data and native sensor data to enable tracking of the activity and health or fitness of the user, wherein the first apparatus is different from the second apparatus, and the first apparatus is configured to be separate from the second apparatus;

wherein the pseudo sensor data is derived and provided to the second apparatus using the first apparatus comprising the radio frequency based tracker during a time interval when the native sensor data representative of the activity of the user that is associated with the second apparatus comprising the health or fitness tracker application is not provided, or when the native sensor data representative of the activity of the user is unavailable to the second apparatus comprising the health or fitness tracker application;

wherein an amount of time between when the native sensor data representative of the activity of the user that is associated with the second apparatus comprising the health or fitness tracker application begins to not be provided to the second apparatus comprising the health or fitness tracker application or when the native sensor data representative of the activity of the user begins to be unavailable to the second apparatus comprising the health or fitness tracker application, and when the pseudo sensor data begins to be provided to the second apparatus comprising the health or fitness tracker application using the first apparatus comprising the radio frequency based tracker, is less than a threshold amount of time.

* * * * *